(12) United States Patent
Kondo

(10) Patent No.: US 8,320,520 B2
(45) Date of Patent: Nov. 27, 2012

(54) X-RAY CT APPARATUS AND METHOD OF CONTROLLING THEREOF

(75) Inventor: Gen Kondo, Otawara (JP)

(73) Assignees: Kabushiki Kaisha Toshiba, Tokyo (JP); Toshiba Medical Systems Corporation, Otawara-shi (JP)

( * ) Notice: Subject to any disclaimer, the term of this patent is extended or adjusted under 35 U.S.C. 154(b) by 231 days.

(21) Appl. No.: 12/872,449

(22) Filed: Aug. 31, 2010

(65) Prior Publication Data
US 2011/0069810 A1 Mar. 24, 2011

(30) Foreign Application Priority Data
Sep. 18, 2009 (JP) ................................. 2009-217728

(51) Int. Cl.
*A61B 6/00* (2006.01)
(52) U.S. Cl. .......................................................... 378/15
(58) Field of Classification Search ................ 378/4, 15, 378/91
See application file for complete search history.

(56) References Cited

U.S. PATENT DOCUMENTS
7,649,972 B2 * 1/2010 Hagiwara et al. ................. 378/4

FOREIGN PATENT DOCUMENTS
JP  6-125889  5/1994

\* cited by examiner

*Primary Examiner* — Jurie Yun
(74) *Attorney, Agent, or Firm* — Oblon, Spivak, McClelland, Maier & Neustadt, L.L.P.

(57) ABSTRACT

In an X-ray Computed Tomography apparatus according to an embodiment, an angle determining unit determines an angle indicating a position of an X-ray radiation unit in a circular orbit at a moment to start radiation after a return of reciprocation, based on a time from a moment of completion of radiation in a movement to a certain direction until a moment to start radiation in a movement after the return, which is a time calculated from scanning conditions. A radiation control unit controls radiation by the X-ray radiation unit so as to start in accordance with the angle determined by the angle determining unit.

6 Claims, 6 Drawing Sheets

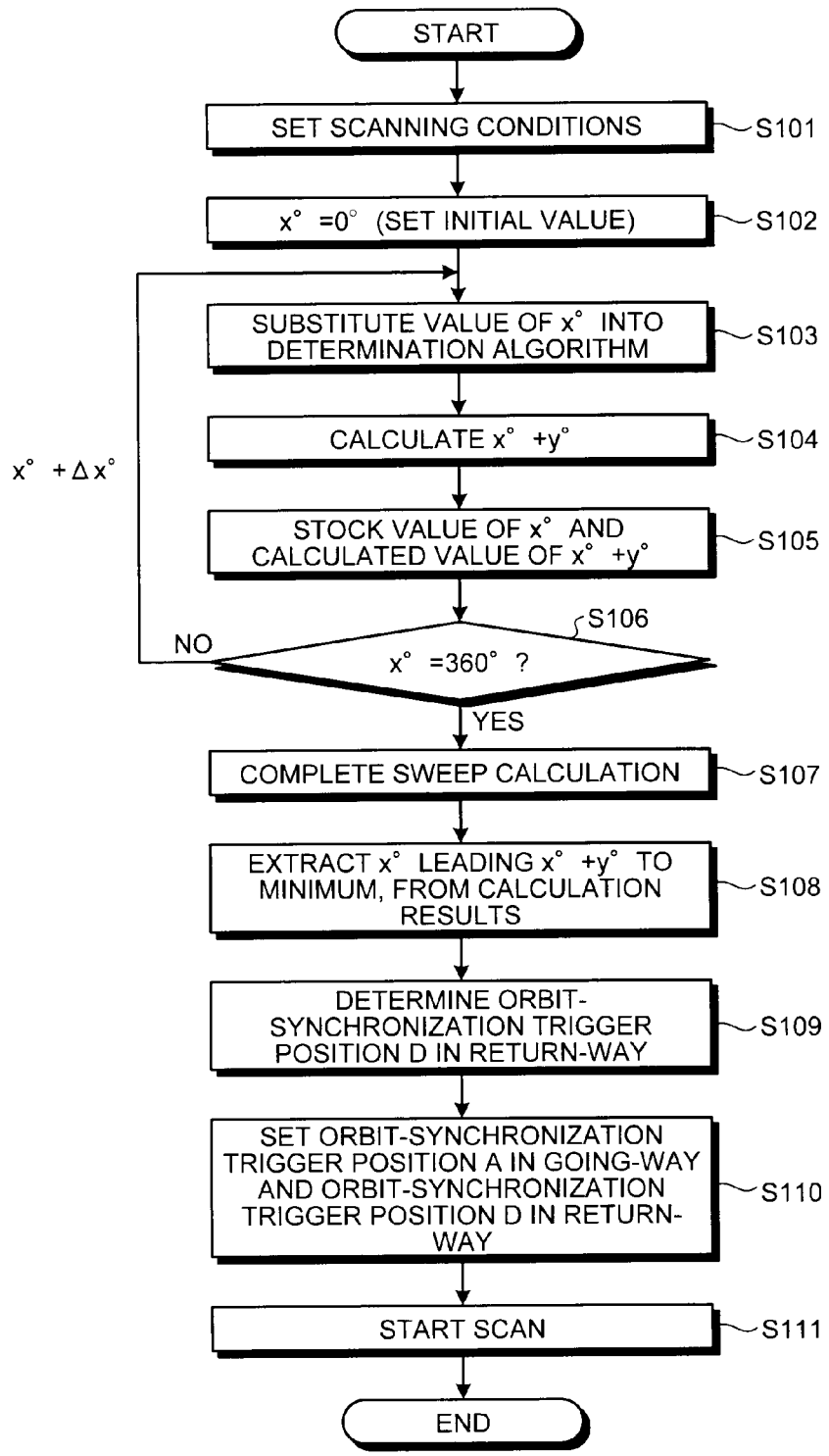

X-RAY CT APPARATUS AND METHOD OF CONTROLLING THEREOF

CROSS-REFERENCE TO RELATED APPLICATIONS

This application is based upon and claims the benefit of priority from Japanese Patent Application No. 2009-217728, filed on Sep. 18, 2009; the entire contents of which are incorporated herein by reference.

FIELD

Embodiments described herein relate generally to an X-ray Computed Tomography (CT) apparatus and a method of controlling the X-ray CT apparatus.

BACKGROUND

Recently, an X-ray Computed Tomography (CT) apparatus uses a scanning method by continuously rotating an X-ray tube in a circular orbit about a subject and continuously reciprocating a top plate (for example, see JP-A H6-1258889 (KOKAI)). According to such scanning method, an X-ray is helically radiated onto the subject, so that tomographic images in a wide area with a good continuity can be obtained. Hereinafter, such scanning method is referred to as a "helical shuttle scan".

According to the helical shuttle scan, orbits of X-rays to be helically radiated onto a subject are controlled so as to be synchronized between a plurality of projection data obtained by scanning in a going way (hereinafter, "going-way scan"), or between a plurality of projection data obtained by scanning in a return way (hereinafter, "return-way scan"). Such control is hereinafter referred to as "orbit synchronization control". For example, conventionally, an X-ray CT apparatus performs orbit synchronization control so as to start radiation of an X-ray based on an origin in a circular orbit (rotational angle 0°) as a starting point in both a going-way scan and a return-way scan. In other words, the X-ray CT apparatus starts radiation in a going-way scan when an X-ray tube is at the rotational angle 0°, and starts radiation in a return-way scan also when the X-ray tube is at the rotational angle 0°.

However, when returning from the going-way scan to the return-way scan, radiation needs to be started after waiting the X-ray tube moves to the position of the origin in the circular orbit (the rotational angle 0°), resulting in a problem that a time loss is large. For example, when radiation in a going-way scan is completed, and a preparation for starting a return-way scan is completed, if the X-ray tube is just past the origin (the rotational angle 0°), the X-ray CT apparatus needs to wait substantially one round until the X-ray tube moves to the origin again, and then to start radiation. It is similar in another going-way scan after the return-way scan is completed.

BRIEF DESCRIPTION OF THE DRAWINGS

FIG. 7 is a flowchart of a process procedure by the X-ray CT apparatus according to the first embodiment.

DETAILED DESCRIPTION

Exemplary embodiments of an X-ray Computed Tomography (CT) apparatus and a method of controlling the X-ray CT apparatus will be explained below in detail with reference to the accompanying drawings.

The X-ray CT apparatus according to an embodiment includes a rotational-movement control unit, an angle determining unit, and a radiation control unit. The rotational-movement control unit continuously rotates an X-ray radiation unit and an X-ray detecting unit in a circular orbit that is formed substantially about a subject placed on a top plate, and continuously reciprocates the top plate in the body axis direction of the subject. The angle determining unit determines an angle indicating the position of the X-ray radiation unit in the circular orbit at a moment to start radiation after a return of the reciprocation, based on a time from a moment of completion of radiation in a movement to a certain direction until a moment to start radiation in a movement after the return, the time being calculated from scanning conditions. The radiation control unit controls radiation by the X-ray radiation unit so as to start in accordance with the angle determined by the angle determining unit.

Figure 1:
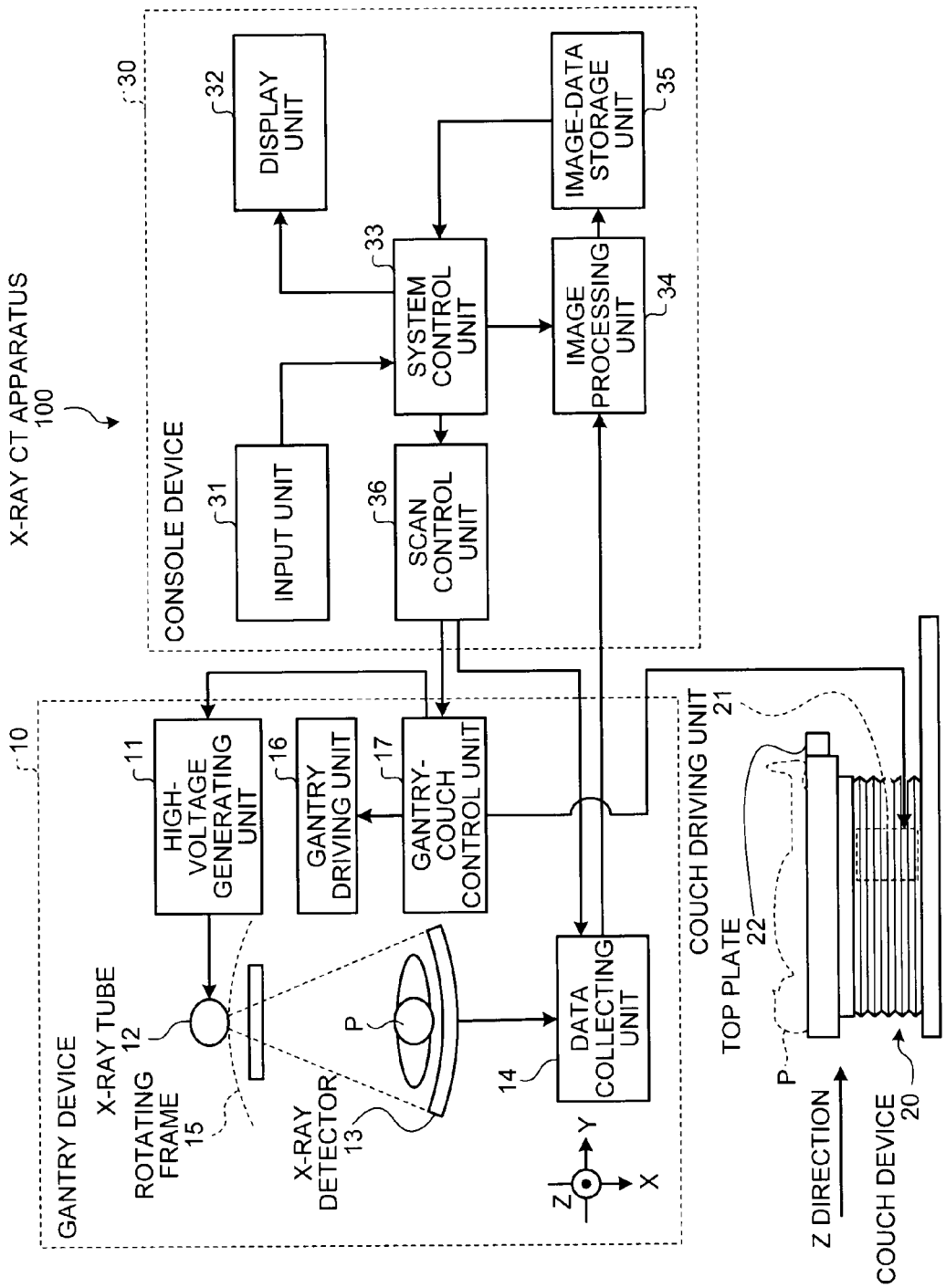
FIG. 1 is a functional block diagram of a configuration of an X-ray Computed Tomography (CT) apparatus according to a first embodiment.

First of all, a configuration of an X-ray CT apparatus 100 according to a first embodiment is explained below with reference to FIGS. 1 to 6. FIG. 1 is a functional block diagram of a configuration of the X-ray CT apparatus 100 according to the first embodiment. As exemplarily shown in FIG. 1, the X-ray CT apparatus 100 according to the first embodiment includes a gantry-couch control unit 17. The gantry-couch control unit 17 preliminarily determines a rotational angle of an X-ray tube 12 when starting radiation in a going-way scan, and a rotational angle of the X-ray tube 12 when starting radiation in a return-way scan. Moreover, the gantry-couch control unit 17 controls a high-voltage generating unit 11, a gantry driving unit 16, and a couch driving unit 21 so as to start radiation by the X-ray tube 12 in accordance with the determined rotational angle. Each of units included in the X-ray CT apparatus 100 according to the first embodiment is explained below, and then the gantry-couch control unit 17 is explained in detail.

As exemplarily shown in FIG. 1, the X-ray CT apparatus 100 according to the first embodiment includes a gantry device 10, a couch device 20, and a console device 30. The gantry device 10 is a device that radiates an X-ray to a subject P, and produces an output to the console device 30 by detecting the X-ray that has passed through the subject P. Specifically, the gantry device 10 includes the high-voltage generating unit 11, the X-ray tube 12, an X-ray detector 13, a data collecting unit 14, a rotating frame 15, the gantry driving unit 16, and the gantry-couch control unit 17.

The high-voltage generating unit 11 supplies a high voltage to the X-ray tube 12 in accordance with the control by the gantry-couch control unit 17. The X-ray tube 12 is a vacuum tube that generates an X-ray with a high voltage supplied by the high-voltage generating unit 11, and radiates the X-ray to the subject P. The X-ray detector 13 detects an X-ray that has passed through the subject P. The data collecting unit 14 creates projection data by using an X-ray detected by the X-ray detector 13. The rotating frame 15 is a frame formed in a toroidal shape, and supports the X-ray tube 12 and the X-ray detector 13 on opposite sides of the subject P.

The gantry driving unit 16 drives a gantry in accordance with the control by the gantry-couch control unit 17. Specifically, the gantry driving unit 16 continuously rotates the rotating frame 15 at high speed by driving a motor, and continuously rotates the X-ray tube 12 and the X-ray detector 13 in a circular orbit about the subject P. The gantry-couch control unit 17 controls the high-voltage generating unit 11, the gantry driving unit 16, and the couch driving unit 21 in accordance with the control by a scan control unit 36, which will described later. The gantry-couch control unit 17 will be described later in detail.

The couch device 20 is a bed on which the subject P as a scan target is to be placed, and includes the couch driving unit 21 and a top plate 22. The couch driving unit 21 continuously reciprocates the top plate 22 in the body axis direction of the subject P by driving the motor in accordance with the control by the gantry-couch control unit 17. The top plate 21 is a plate on which the subject P is to be placed.

The console device 30 receives an operation of the X-ray CT apparatus 100 by an operator, and reconstructs an image from projection data collected by the gantry device 10. Specifically, the console device 30 includes an input unit 31, a display device 32, a system control unit 33, an image processing unit 34, an image-data storage unit 35, and the scan control unit 36.

The input unit 31 is a mouse, a keyboard, and the like, and is used for the operator to input an instruction to the X-ray CT apparatus 100. For example, the input unit 31 receives setting of scanning conditions. The display device 32 is a display device, such as a Liquid Crystal Display (LCD), and displays various information. For example, the display device 32 displays an image stored by the image-data storage unit 35, and a Graphical User Interface (GUI) for receiving various instructions from the operator.

The system control unit 33 is an integrated circuit, such as an Application Specific Integrated Circuit (ASIC) or a Field Programmable Gate Array (FPGA), or an electronic circuit, such as a Central Processing Unit (CPU), or a Micro Processing Unit (MPU). Specifically, the system control unit 33 controls the gantry device 10, the couch device 20, and the console device 30, thereby performing overall control of the X-ray CT apparatus 100. For example, the system control unit 33 controls the scan control unit 36, and causes it to collect projection data. Moreover, for example, the system control unit 33 controls the image processing unit 34, and causes it to reconstruct an image from projection data.

The image processing unit 34 is an integrated circuit, such as an ASIC or an FPGA, or an electronic circuit, such as a CPU or an MPU, and performs various processing on projection data created by the data collecting unit 14. Specifically, the image processing unit 34 performs preprocessing, such as sensitivity correction, on projection data created by the data collecting unit 14, reconstructs an image based on reconstruction conditions instructed by the system control unit 33, and stores the reconstructed image into the image-data storage unit 35.

The image-data storage unit 35 is a semiconductor memory device, such as a Random Access Memory (RAM), a Read-Only Memory (ROM), or a flash memory, a hard disk, or an optical disk; and stores an image reconstructed by the image processing unit 34. The scan control unit 36 is an integrated circuit, such as an ASIC or an FPGA, or an electronic circuit, such as a CPU or an MPU, and controls the gantry-couch control unit 17 based on scanning conditions instructed by the system control unit 33.

Figure 2:
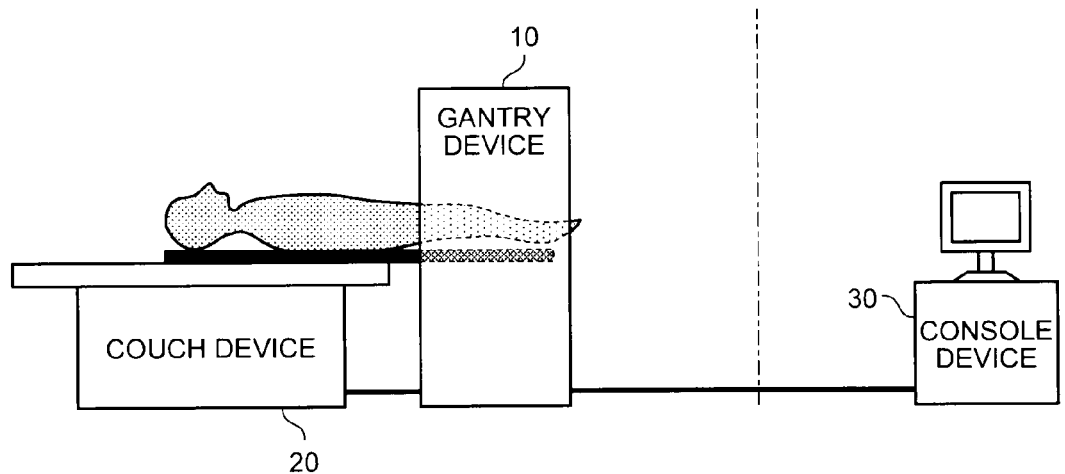
FIG. 2 is a general view of the X-ray CT apparatus according to the first embodiment.

FIG. 2 is a general view of the X-ray CT apparatus 100 according to the first embodiment. The gantry device 10, the couch device 20, and the console device 30 are placed as exemplarily shown in FIG. 2. A broken line shown in FIG. 2 denotes a boundary between a scanner room in which the gantry device 10 and the couch device 20 are placed, and a console room in which the console device 30 is placed. An arrow with a reference letter a shown in FIG. 2 denotes the body direction of the subject P. According to the first embodiment, the top plate 22 continuously reciprocates to a first direction (for example, a going-way direction) in parallel with the body axis direction of the subject P, and a second direction (for example, a return-way direction) opposite to the first direction.

Figure 3:
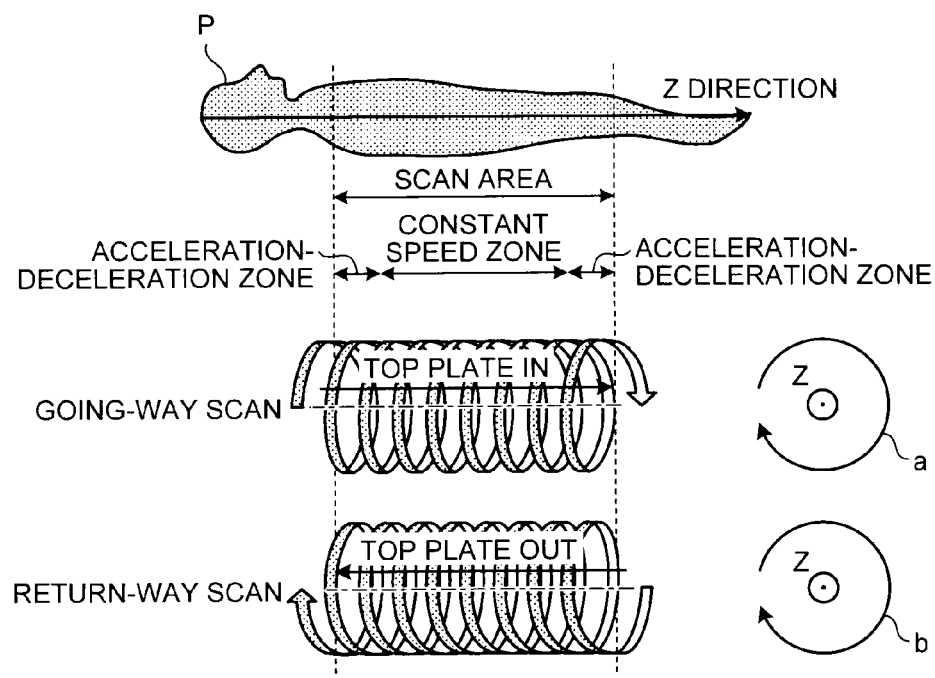
FIG. 3 is a schematic diagram for explaining a helical shuttle scan according to the first embodiment.

FIG. 3 is a schematic diagram for explaining a helical shuttle scan according to the first embodiment. The helical shuttle scan is a scanning method by continuously rotating the X-ray tube 12 in the circular orbit about the subject P, and continuously reciprocating the top plate 22. According to the helical shuttle scan, as exemplarily shown in FIG. 3, an X-ray is helically radiated onto the subject P. Although the subject P and spirals are separately shown in FIG. 3 for convenience of explanation, an X-ray is helically radiated so as to surround the subject P.

As exemplarily shown in FIG. 3, it is assumed that along the body axis direction of the subject P, a direction of an arrow from the head toward the foot is referred to as a direction Z, a process of moving the top plate 22 to the same direction as the direction Z is referred to as a going-way scan, and a process of moving it to the direction opposite to the Z direction is referred to as a return-way scan. An arrow of "top plate IN" exemplarily shown in FIG. 3 denotes the direction to which the top plate 22 moves in a going-way scan, and an arrow of "top plate OUT" denotes the direction to which the top plate 22 moves in a return-way scan.

The X-ray CT apparatus 100 according to the first embodiment moves the top plate 22 at a constant speed in a constant speed zone set within a scan area, and accelerates or decelerates the movement speed of the top plate 22 in each acceleration-deceleration zone. In other words, the X-ray CT apparatus 100 stops the top plate 22 by decelerating the movement speed of the top plate 22 in the acceleration-deceleration zone, and reverses the movement direction of the top plate 22; and when the top plate 22 is returned, the X-ray CT apparatus 100 accelerates the movement speed of the top plate 22 in the acceleration-deceleration zone. Arrows of a reference letter "a" and a reference letter "b" shown in FIG. 3 denote rotational directions of the X-ray tube 12. Although FIG. 3 depicts an example that acceleration-deceleration zones are provided within a scan area, it is not limited to this, and also can be similarly applied to a case where an acceleration-deceleration zone is provided outside the scan area.

Figure 4:
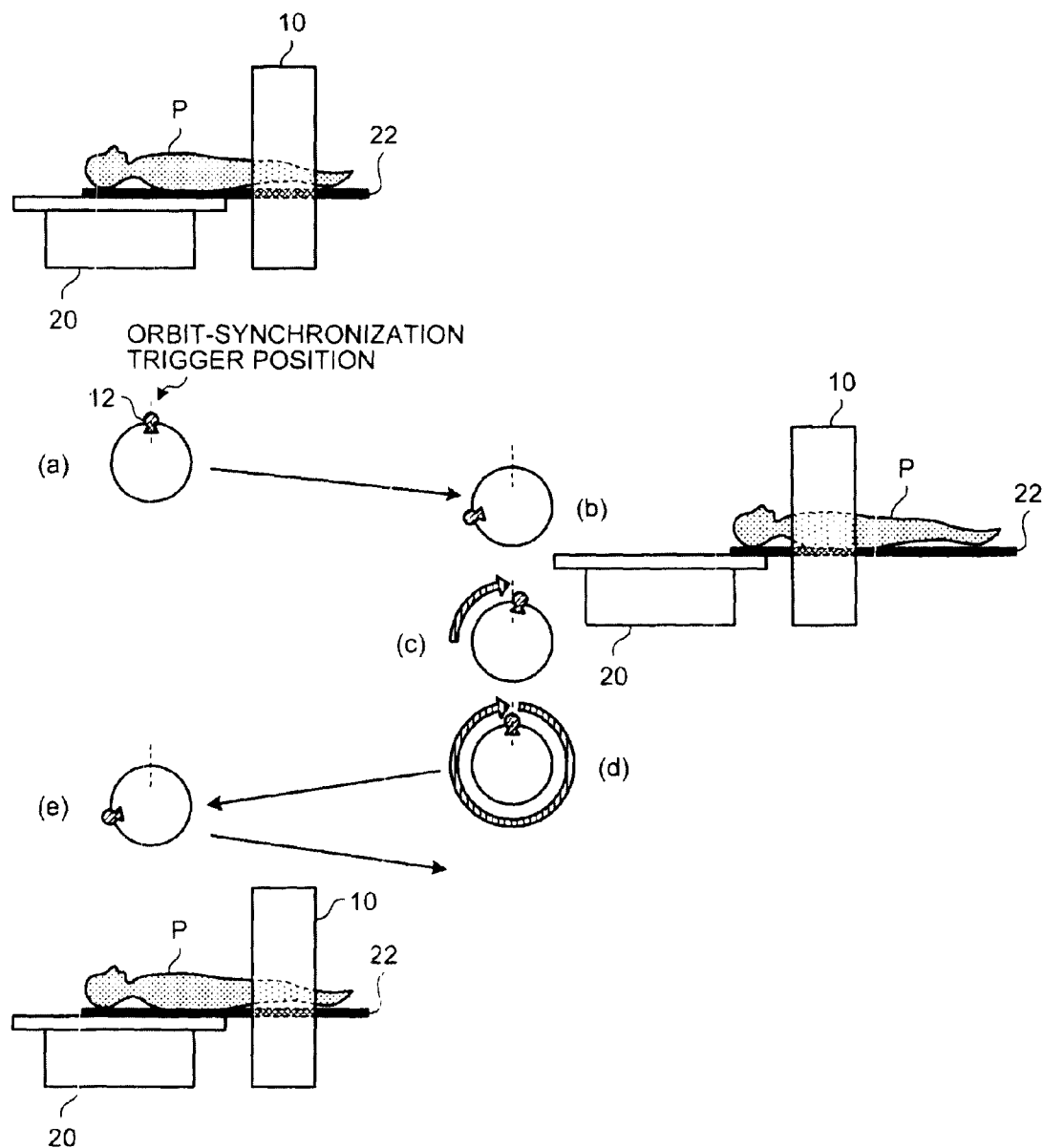
FIG. 4 is a schematic diagram for explaining conventional orbit synchronization control.

According to a conventional helical shuttle scan, orbit synchronization control is performed so as to start radiation of an X-ray based on an origin in a circular orbit (rotational angle 0°) as a starting point in both a going-way scan and a return-way scan. FIG. 4 is a schematic diagram for explaining conventional orbit synchronization control.

An "orbit-synchronization trigger position" exemplarily shown in a section (a) in FIG. 4 indicates the position of the X-ray tube 12 when starting radiation. According to the conventional helical shuttle scan, as exemplarily shown in FIG. 4, for example, radiation is started in a going-way scan when the X-ray tube 12 is at the rotational angle 0° (see the section (a)

in FIG. 4), and radiation is started in a return-way scan also when the X-ray tube 12 is at the rotational angle 0° (see a section (d) in FIG. 4).

Consequently, as exemplarily shown in FIG. 4, for example, there is a case where when radiation in the going-way scan is completed (see a section (b) in FIG. 4), and a preparation for starting a return-way scan is completed, the X-ray tube 12 is positioned in a rotational angle just past the origin (see a section (c) in FIG. 4). In such case, the X-ray CT apparatus 100 needs to wait substantially one round until the X-ray tube 12 moves to the origin again (see the section (d) in FIG. 4), and then to start radiation. It is similar in another going-way scan after the return-way scan is completed (see a section (e) in FIG. 4).

Figure 5:
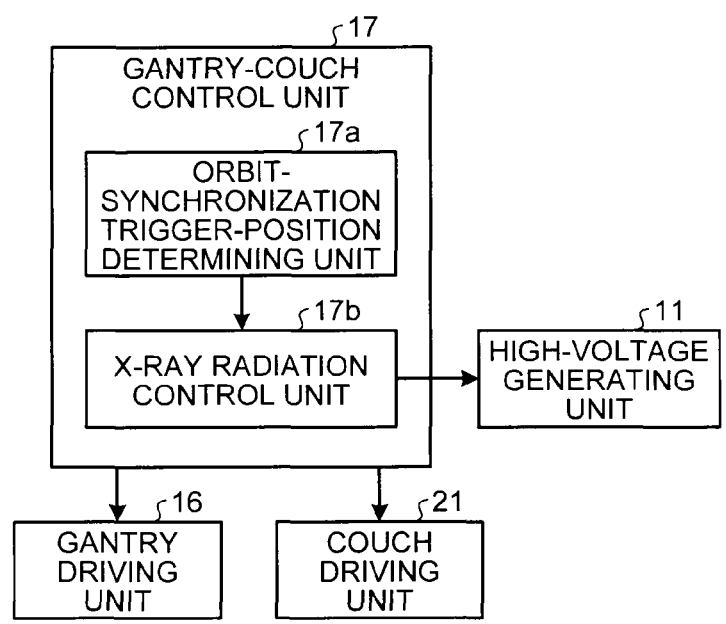
FIG. 5 is a functional block diagram of a configuration of a gantry-couch control unit according to the first embodiment.

The gantry-couch control unit 17 according to the first embodiment is explained below. FIG. 5 is a functional block diagram of a configuration of the gantry-couch control unit 17 according to the first embodiment. The gantry-couch control unit 17 according to the first embodiment continuously rotates the X-ray tube 12 and the X-ray detector 13 in the circular orbit substantially about the subject P placed on the top plate 22, by controlling the gantry driving unit 16. Moreover, the gantry-couch control unit 17 continuously reciprocates the top plate 22 by controlling the couch driving unit 21. In this way, the gantry-couch control unit 17 controls the gantry driving unit 16 and the couch driving unit 21, thereby achieving a shuttle helical scan.

As exemplarily shown in FIG. 5, the gantry-couch control unit 17 according to the first embodiment particularly includes an orbit-synchronization trigger-position determining unit 17a and an X-ray radiation control unit 17b. By including the orbit-synchronization trigger-position determining unit 17a and the X-ray radiation control unit 17b, the gantry-couch control unit 17 according to the first embodiment optimizes orbit synchronization control, and reduces a returning time when returning between a going-way scan and a return-way scan. This is specifically explained below.

The orbit-synchronization trigger-position determining unit 17a preliminarily determines an orbit-synchronization trigger position (going-way) when starting radiation in a going-way scan, and an orbit-synchronization trigger position (return-way) when starting radiation in a return-way scan, based on a waiting time when returning. Specifically, when receiving scanning conditions from the scan control unit 36, the orbit-synchronization trigger-position determining unit 17a preliminarily performs a calculation of determining the orbit-synchronization trigger position (going-way) and the orbit-synchronization trigger position (return-way) by using the received scanning conditions, and notifies the X-ray radiation control unit 17b of the orbit-synchronization trigger position (going-way) and the orbit-synchronization trigger position (return-way) both of which are determined by the calculation.

The X-ray radiation control unit 17b controls radiation by the X-ray tube 12 and a movement of the top plate 22 so as to start in accordance with the orbit-synchronization trigger position (going-way) and the orbit-synchronization trigger position (return-way) that are preliminarily determined. Specifically, when receiving the orbit-synchronization trigger position (going-way) and the orbit-synchronization trigger position (return-way) from the orbit-synchronization trigger-position determining unit 17a, the X-ray radiation control unit 17b controls the high-voltage generating unit 11 so as to start radiation by the X-ray tube 12 in accordance with the received orbit-synchronization trigger position (going-way) and the received orbit-synchronization trigger position (return-way). Moreover, simultaneously, the X-ray radiation control unit 17b starts a movement of the top plate 22 so as to synchronize with the start of the radiation by the X-ray tube 12.

Figure 6:
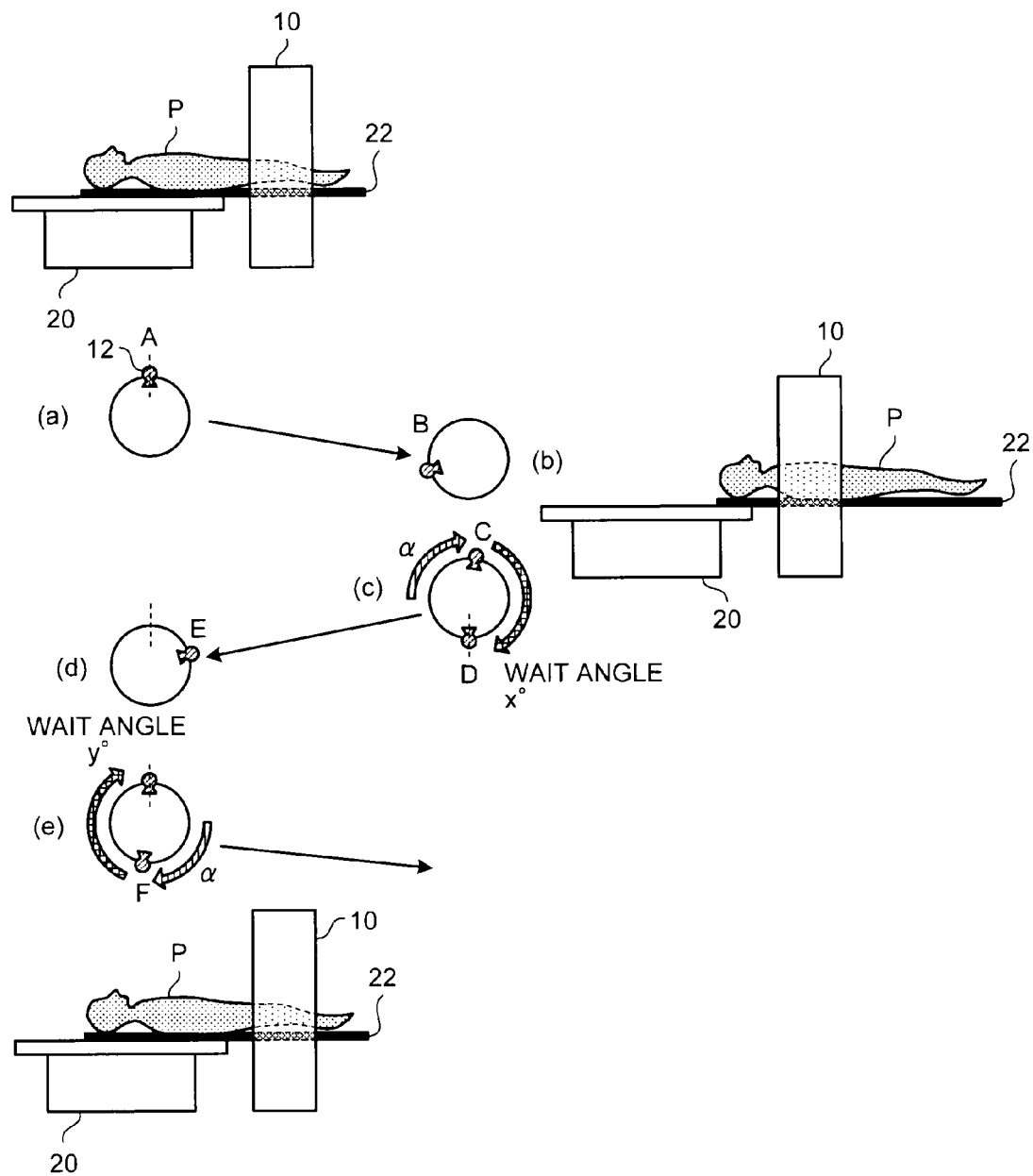
FIG. 6 is a schematic diagram for explaining optimization of orbit synchronization control according to the first embodiment.

Optimization of orbit synchronization control is explained below. FIG. 6 is a schematic diagram for explaining optimization of orbit synchronization control according to the first embodiment. The orbit-synchronization trigger-position determining unit 17a according to the first embodiment determines the orbit-synchronization trigger position (going-way) and the orbit-synchronization trigger position (return-way) so as to minimize the sum of a differential angle in a rotational direction between a rotational angle at completion of radiation in a going-way scan and the orbit-synchronization trigger position (return-way), and a differential angle in a rotational direction between a rotational angle at completion of radiation in a return-way scan and the orbit-synchronization trigger position (going-way).

In other words, explaining this with reference to FIG. 6, a rotational angle A shown in a section (a) in FIG. 6 indicates the orbit-synchronization trigger position (going-way). A rotational angle B shown in a section (b) in FIG. 6 indicates a rotational angle of the X-ray tube 12 when radiation in a going-way scan is completed. A rotational angle C shown in a section (c) in FIG. 6 indicates a rotational angle of the X-ray tube 12 when a preparation for starting a return-way scan is completed. A letter a in the section (c) in FIG. 6 indicates a rotational angle by which the X-ray tube 12 moves during a preparation time for starting the return-way scan.

A rotational angle D shown in the section (c) in FIG. 6 indicates the orbit-synchronization trigger position (return-way). A rotational angle E shown in a section (d) in FIG. 6 indicates a rotational angle of the X-ray tube 12 when radiation in a return-way scan is completed. A rotational angle F shown in a section (e) in FIG. 6 indicates a rotational angle when a preparation for starting a going-way scan is completed. A letter a in the section (e) in FIG. 6 indicates a rotational angle by which the X-ray tube 12 moves during a preparation time for starting the going-way scan.

Moreover, in FIG. 6, an angle from a rotational angle at completion of a preparation for starting a next scan to an orbit-synchronization trigger position (hereinafter, "wait angle") is "x°" shown in the section (c) in FIG. 6 when returning from a going-way scan to a return-way scan, and it is "y°" shown in the section (e) in FIG. 6 when returning from a return-way scan to a going-way scan.

Accordingly, as the rotational angle A and the rotational angle D are preliminarily determined so as to minimize "x°+y°", which is the sum of the wait angles, and the control is performed so as to start radiation by the X-ray tube 12 in accordance with the rotational angle A and the rotational angle D that are preliminarily determined, a returning time when returning between a going-way scan and a return-way scan can be reduced.

An algorithm of determining the rotational angle A and the rotational angle D so as to minimize "x°+y°", which is the sum of the wait angles, is explained below. As a constant to be used in the determination algorithm, the orbit-synchronization trigger-position determining unit 17a uses "V views" denoting the number of views to be collected in one way (a going-way scan or a return-way scan), "v views" denoting the number of views required to reconstruct one piece of tomogram, "r rot/sec" denoting a rotational speed of the X-ray tube 12, and "q seconds" denoting a preparation time for starting a next scan (hereinafter, "a setup time between scans").

For example, suppose the number of views to be collected in one way is 20,000 views, and the number of views required to reconstruct one piece of tomogram is 1,000 views. In this case, 1,000 views are collected per rotation of the X-ray tube 12; it is calculated from 20,000 views/1,000 views=20 so that the X-ray tube 12 rotates 20 times in one way.

On the other hand, for example, suppose the number of views to be collected in one way is 20,500 views, and the number of views required to reconstruct one piece of tomogram is 1,000 views. In this case, 1,000 views are collected per rotation of the X-ray tube 12; it is calculated from 20,500 views/1,000 views=20 so that the X-ray tube 12 rotates 20.5 times in one way. In this case, when the orbit-synchronization trigger position (going-way) is "0°", it means that the going-way scan is completed at the rotational angle of "180°", exceeding by 0.5 rotation.

Regarding the number of views to be collected in one way, the number of views required to reconstruct one piece of tomogram, and the rotational speed of the X-ray tube 12, the orbit-synchronization trigger-position determining unit 17a uses respective values given from scanning conditions received from the scan control unit 36. Moreover, the orbit-synchronization trigger-position determining unit 17a uses a substantially constant value of the setup time between scans regardless of the scanning conditions. The setup time between scans is, for example, a processing time of a program, and can be calculated from, for example, the number of steps of the program.

The orbit-synchronization trigger-position determining unit 17a performs calculations according to the determination algorithm by using the above constants and Expression (1) to Expression (6) described below. Reference letters "mod" denote a residual obtained by dividing a numerator by a denominator. To express the value of a rotational angle with a number equal to or less than 360°, a residual is calculated by dividing the rotational angle by 360°.

To begin with, the orbit-synchronization trigger-position determining unit 17a determines the rotational angle A indicating the orbit-synchronization trigger position (going-way) to "0°", and substitutes it into Expression (1). Moreover, the orbit-synchronization trigger-position determining unit 17a substitutes V views and v views received from the scan control unit 36 into Expression (1). The orbit-synchronization trigger-position determining unit 17a then calculates Expression (1), thereby obtaining the rotational angle B of the X-ray tube 12 at the moment of completion of radiation in the going-way scan.

$$B = \mod\left(\frac{A + 360\frac{V}{v}}{360}\right) \quad (1)$$

The orbit-synchronization trigger-position determining unit 17a then substitutes the rotational angle B obtained from the above Expression (1), r rot/sec received from the scan control unit 36, and q seconds of the setup time between scans into Expression (2). The orbit-synchronization trigger-position determining unit 17a then calculates Expression (2), thereby obtaining the rotational angle C of the X-ray tube 12 at the moment of completion of a preparation for starting a return-way scan.

$$C = \mod\left(\frac{B + 360r \cdot q}{360}\right) \quad (2)$$

Subsequently, the orbit-synchronization trigger-position determining unit 17a substitutes the rotational angle C obtained from the above Expression (2), and the initial value "0°" of the wait angle x° into Expression (3). The orbit-synchronization trigger-position determining unit 17a then calculates Expression (3), thereby obtaining the rotational angle D indicating the orbit-synchronization trigger position (return-way).

$$D = \mod\left(\frac{C + x}{360}\right) \quad (3)$$

Moreover, the orbit-synchronization trigger-position determining unit 17a substitutes the rotational angle D indicating the orbit-synchronization trigger position (return-way) obtained from the above Expression (3), and V views and v views received from the scan control unit 36 into Expression (4). The orbit-synchronization trigger-position determining unit 17a then calculates Expression (4), thereby obtaining the rotational angle E of the X-ray tube 12 at the moment of completion of radiation in the return-way scan.

$$E = \mod\left(\frac{D + 360\frac{V}{v}}{360}\right) \quad (4)$$

The orbit-synchronization trigger-position determining unit 17a then substitutes the rotational angle E obtained from the above Expression (4), r rot/sec received from the scan control unit 36, and q seconds of the setup time between scans into Expression (5). The orbit-synchronization trigger-position determining unit 17a then calculates Expression (5), thereby obtaining the rotational angle F of the X-ray tube 12 at completion of a preparation for starting a return-way scan.

$$F = \mod\left(\frac{E + 360r \cdot q}{360}\right) \quad (5)$$

Subsequently, the orbit-synchronization trigger-position determining unit 17a substitutes the rotational angle F obtained from the above Expression (5), and "0°" of the rotational angle A indicating the orbit-synchronization trigger position (going-way) into Expression (6). The orbit-synchronization trigger-position determining unit 17a calculates Expression (6), thereby obtaining the wait angle y°.

$$A = \mod\left(\frac{F + y}{360}\right) \quad (6)$$

Through a series of calculations of the above Expression (1) to Expression (6), the orbit-synchronization trigger-position determining unit 17a obtains the wait angle y° when the wait angle x° is "0°", thereby obtaining "x°+y°", which is the sum of the wait angles. The orbit-synchronization trigger-position determining unit 17a then repeatedly performs a sweep calculation, for example, by increasing the wait angle x° by 1°, and searches for a wait angle x° leading "x°+y°" to a minimum, which is the sum of the wait angles. The orbit-synchronization trigger-position determining unit 17a then substitutes the searched wait angle x° into Expression (3), thereby determining the rotational angle D indicating the orbit-synchronization trigger position (return-way).

A process procedure by the X-ray CT apparatus 100 according to the first embodiment is explained below with reference to FIG. 7. FIG. 7 is a flowchart of a process procedure by the X-ray CT apparatus 100 according to the first embodiment.

As shown in FIG. 7, to begin with, the X-ray CT apparatus 100 sets scanning conditions into the determination algorithm (Step S101). For example, when the operator inputs scanning conditions to the X-ray CT apparatus 100 by using the input unit 31, the input scanning conditions are transmitted to the scan control unit 36 via the system control unit 33. The scan control unit 36 extracts, "V views" denoting the number of views to be collected in one way, "v views" denoting the number of views required to reconstruct one piece of tomogram, and "r rot/sec" denoting a rotational speed of the X-ray tube 12, from the received scanning conditions, and transmits them to the orbit-synchronization trigger-position determining unit 17a of the gantry-couch control unit 17. Moreover, the scan control unit 36 transmits also "q seconds" denoting a setup time between scans to the orbit-synchronization trigger-position determining unit 17a. In this way, the orbit-synchronization trigger-position determining unit 17a sets "V views", "v views", "r rot/sec", and "q seconds" in the determination algorithm.

The orbit-synchronization trigger-position determining unit 17a then sets an initial value of the wait angle x° to "0°" (Step S102). Subsequently, in addition to the values set at Steps S101 and S102, the orbit-synchronization trigger-position determining unit 17a sets the rotational angle A indicating the orbit-synchronization trigger position (going-way) to "0°", substitutes it into the determination algorithm expressed by Expression (1) to Expression (6) described above, and calculates "x°+y°", which is the sum of the wait angles (Steps S103 and S104).

The orbit-synchronization trigger-position determining unit 17a then temporarily stocks the value set in the wait angle x° at Step S103, and the calculated value of "x°+y°" as the sum of the wait angles calculated at Step S104, into a storage unit, such as a memory (Step S105).

The orbit-synchronization trigger-position determining unit 17a then determines whether the wait angle x° is "360°" (Step S106); if it is not "360°" (No at Step S106), the orbit-synchronization trigger-position determining unit 17a sets a new wait angle x° to a value that the new wait angle x° is added with Δx°, for example, "1°", and then returns to the processing at Step S103.

In other words, for example, the orbit-synchronization trigger-position determining unit 17a uses the value of "1°" as the wait angle x°, substitutes it again into the determination algorithm expressed in Expression (1) to Expression (6) described above, calculates "x°+y°", which is the sum of the wait angles (Steps S103 and S104); and stocks the calculated value (Step S105).

In this way, according to the first embodiment, because a value added with "1°" as Δx° becomes a new wait angle x°, the processing at Steps S103 to S105 is repeated 360 times, until it is determined at Step S106 that the wait angle x° is "360°".

When it is determined at Step S106 that the wait angle x° is "360°" (Yes at Step S106); the orbit-synchronization trigger-position determining unit 17a completes the sweep calculation (Step S107); and then extracts a wait angle x° leading "x°+y°" to a minimum, which is the sum of the wait angles, is minimized, from the calculation results of 360 times stocked at Step S105 (Step S108). In other words, the orbit-synchronization trigger-position determining unit 17a searches the calculation results stocked at Step S105, and searches for a wait angle x° stored by being associated with the minimum "x°+y°".

The orbit-synchronization trigger-position determining unit 17a then substitutes the searched wait angle x° into Expression (3) described above, thereby determining the rotational angle D indicating the orbit-synchronization trigger position (return-way) (Step S109).

Subsequently, the orbit-synchronization trigger-position determining unit 17a notifies the rotational angle A indicating the orbit-synchronization trigger position (going-way) and the rotational angle D indicating the orbit-synchronization trigger position (return-way) to the X-ray radiation control unit 17b; and then the X-ray radiation control unit 17b sets the received rotational angle A and the received rotational angle D (Step S110).

After that, a helical shuttle scan is started in the X-ray CT apparatus 100 (Step S111); the X-ray radiation control unit 17b controls the high-voltage generating unit 11 so as to start radiation by the X-ray tube 12 in accordance with the rotational angle A and the rotational angle D notified from the orbit-synchronization trigger-position determining unit 17a.

The values and the process procedure described above are only an example. For example, although it is assumed that the rotational angle A indicating the orbit-synchronization trigger position (going-way) is set to "0°", it is not limited to this, and can be another rotational angle other than "0°". Moreover, for example, although the method by adding "1°" as Δx° is explained above, it is not limited to this, and can be a method by adding by another unit value. Furthermore, for example, Expression (1) to Expression (6) are only an example; and for example, a method having a meaning similar to Expression (1) to Expression (6) and calculating by using other expressions modified from Expression (1) to Expression (6) can be acceptable. Moreover, for example, although the method by calculating rotational angles and calculating a sum of wait angles is explained above according to Expression (1) to Expression (6), it is not limited to this, and can be similarly applied to a method by calculating in expressions in which a rotational angle is replaced with a time, and a wait angle is replaced with a wait time (wafting time).

Furthermore, for example, the above sweep calculation is only an example, and another method is acceptable as long as a method of optimizing the orbit-synchronization trigger position (going-way) and the orbit-synchronization trigger position (return-way) in order to reduce a waiting time when returning. The "optimization" does not necessarily means that a waiting time needs to be the "shortest time", so that the waiting time does not need to be the "shortest time" as long as it is optimized in accordance with a style of operation.

As described above, the X-ray CT apparatus 100 according to the first embodiment continuously rotates the X-ray tube 12 and the X-ray detector 13 in the circular orbit substantially about the subject P placed on the top plate 22, and continuously reciprocates the top plate 22 in the body axis direction of the subject P. The gantry-couch control unit 17 then determines an angle indicating the position of the X-ray tube 12 in the circular orbit at a moment to start radiation after a return of the reciprocation, based on a time from a moment of completion of radiation in a movement to a certain direction until a moment to start radiation in a movement after the return, which is a time calculated from scanning conditions. Specifically, the gantry-couch control unit 17 determines the orbit-synchronization trigger position (going-way) and the orbit-synchronization trigger position (return-way) so as to minimize the sum of a differential angle in a rotational direction between a rotational angle at completion of radiation in a going-way scan and the orbit-synchronization trigger position (return-way), and a differential angle in a rotational direction between a rotational angle at completion of radiation in a return-way scan and the orbit-synchronization trigger position (going-way), the sum being a value calculated from the scanning conditions. The gantry-couch control unit 17 then controls the high-voltage generating unit 11 so as to start radiation by the X-ray tube 12 in accordance with the determined angle.

In this way, according to the first embodiment, because a waiting time when returning between a going-way scan and a return-way scan is preliminarily calculated to be the shortest, and then radiation by the X-ray tube 12 is started based on the determined orbit-synchronization trigger position (going-way) and the determined orbit-synchronization trigger position (return-way), the orbit synchronization control can be optimized, and a returning time can be reduced.

Consequently, as the orbit synchronization control optimized in this way is repeated in the helical shuttle scan, an effect of reduction is notably observed in a total of returning times, and also there is an effect that temporal resolution of each image acquired in each of a going-way scan and a return-way scan is improved. Furthermore, there is an effect that temporal resolution of a subtraction image between an image acquired in a going-way scan and an image acquired in a return-way scan is improved.

In addition to the first embodiment, various different embodiments can be implemented.

For example, the first embodiment is explained above by assuming that the gantry-couch control unit 17 included in the gantry device 10 performs the processing of determining the orbit-synchronization trigger position (going-way) and the orbit-synchronization trigger position (return-way). However, it is not limited to this. For example, the processing of determining the orbit-synchronization trigger position (going-way) and the orbit-synchronization trigger position (return-way) can be performed by the side of the console device 30 (for example, the scan control unit 36). In such case, the gantry-couch control unit 17 receives the predetermined orbit-synchronization trigger position (going-way) the predetermined orbit-synchronization trigger position (return-way) as a command together with other scanning conditions, and then controls the high-voltage generating unit 11 by using the received orbit-synchronization trigger position (going-way) and the received orbit-synchronization trigger position (return-way).

Moreover, the first embodiment uses an example of a helical shuttle scan that an X-ray is radiated onto the subject P while moving the top plate 22, it is not limited to this. For example, it can be applied to a scanning method by which reciprocations are further repeated in a certain range in a scanning method of synchronizing orbits of respective half reconstruction scan by continuously performing the following steps: while stopping the top plate 22, performing a half reconstruction scan on the subject P; after moving the top plate 22 by an extent equivalent to the width of the detector, similarly performing a half reconstruction scan; and then moving the top plate 22. The half reconstruction scan is a method of reconstructing an image with collected data obtained through a rotation equivalent to the sum of 180 degrees and a detector fan angle.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. An X-ray Computed Tomography (CT) apparatus, comprising:
    a rotational-movement control unit that continuously rotates an X-ray radiation unit and an X-ray detecting unit in a circular orbit that is formed substantially about a subject placed on a top plate, and continuously reciprocates the top plate in a body axis direction of the subject;
    an angle determining unit that determines an angle indicating a position of the X-ray radiation unit in the circular orbit at a moment to start radiation after a return of reciprocation, based on a time from a moment of completion of radiation in a movement to a certain direction until a moment to start radiation in a movement after the return, the time being calculated from scanning conditions; and
    a radiation control unit that controls radiation by the X-ray radiation unit so as to start in accordance with the angle determined by the angle determining unit.

2. The X-ray CT apparatus according to claim 1, wherein the rotational-movement control unit reciprocates the top plate continuously in a first direction and in a second direction that is opposite to the first direction; and
    the angle determining unit determines a first angle indicating a position of the X-ray radiation unit in the circular orbit at a moment to start radiation in a movement to the first direction, and a second angle indicating a position of the X-ray radiation unit in the circular orbit at a moment to start radiation in a movement to the second direction, so as to minimize a sum of a differential angle in a rotational direction between an angle at completion of radiation in a movement to the first direction and the second angle, and a differential angle in a rotational direction between an angle at completion of radiation in a movement to the second direction and the first angle, the sum being a value calculated from the scanning conditions.

3. The X-ray CT apparatus according to claim 1, wherein the angle determining unit further uses a preparation time for starting radiation in a movement after a return, for determination of the angle.

4. A method of controlling an X-ray CT apparatus comprising:
    rotating continuously an X-ray radiation unit and an X-ray detecting unit in a circular orbit that is formed substantially about a subject placed on a top plate, and continuously reciprocating the top plate in a body axis direction of the subject;
    determining an angle indicating a position of the X-ray radiation unit in the circular orbit at a moment to start radiation after a return of reciprocation, based on a time from a moment of completion of radiation in a movement to a certain direction until a moment to start radiation in a movement after the return, which is a time calculated from scanning conditions; and
    controlling radiation by the X-ray radiation unit so as to start in accordance with the angle determined.

5. The method according to claim 4, further comprising:
    reciprocating the top plate continuously in a first direction and in a second direction that is opposite to the first direction; and
    determining a first angle indicating a position of the X-ray radiation unit in the circular orbit at a moment to start radiation in a movement to the first direction, and a second angle indicating a position of the X-ray radiation unit in the circular orbit at a moment to start radiation in a movement to the second direction, so as to minimize a sum of a differential angle in a rotational direction between an angle at completion of radiation in a movement to the first direction and the second angle, and a differential angle in a rotational direction between an angle at completion of radiation in a movement to the second direction and the first angle, the sum being a value calculated from the scanning conditions.

6. The method according to claim 4, wherein a preparation time for starting radiation in a movement after a return is further used for the determining the angle.

* * * * *